United States Patent [19]

Berg et al.

[11] Patent Number: 5,645,991
[45] Date of Patent: Jul. 8, 1997

[54] TRANSPOSON-CONTAINING DNA CLONING VECTOR AND USES THEREOF

[75] Inventors: Claire M. Berg, W. Willington, Conn.; Douglas E. Berg, St. Louis, Mo.; Gan Wang, Storrs, Conn.

[73] Assignees: Univ. of Connecticut, Storrs, Conn.; Washington University, St. Louis, Mo.

[21] Appl. No.: 403,582

[22] Filed: Mar. 14, 1995

Related U.S. Application Data

[63] Continuation-in-part of Ser. No. 57,314, May 4, 1993, abandoned.

[51] Int. Cl.$^6$ ................................................. C12N 15/00
[52] U.S. Cl. ................ 435/6; 435/172.3; 435/252.3; 435/252.33; 435/320.1
[58] Field of Search .................. 435/172.3, 172.1, 435/320.1, 6, 252.3, 252.33; 536/23.1, 24.1

[56] References Cited

U.S. PATENT DOCUMENTS 4,716,105  12/1987  Mizuuchi et al. .................. 435/5
5,137,829  8/1992   Nag et al. ..................... 435/320.1

OTHER PUBLICATIONS

G. Wang, R.W. Blakesley, D.E. Berg, L.Y. Lee and C.M. Berg. "Efficient DNA Sequencing of Cosmid Clones: pJANUS 'Deletion Factory' Vectors". Genome Sequencing and Analysis Conference IV, Hilton Head, SC, 1992.

C.M. Berg, D.E. Berg and E.A. Groisman. "Transposable Elements and the Genetic Engineering of Bacteria". In: Mobile DNA, D.F. Berg and M. Howe, eds., American Society for Microbiology, Washington, DC, pp. 879–925, 1989.

A. Ahmed. "Use of transposon–Promoted Deletions in DNA Sequence Analysis". Methods in Enzymology, vol. 155, pp. 177–204, 1987.

Glaser et al. (1989) Somatic Cell and Molecular Genetics, vol. 15, pp. 477–501.

Sambrook et al. (1989) Molecular Cloning: A Laboratory Manual (Cold Spring Harbor Lab, Cold Spring Harbor) pp. 1.1–1.110, 3.1–3.58, 10.1–10.70.

Groisman et al. (1984) Proceedings of the National Academy of Sciences, vol. 81, pp. 1480–1483.

Neidhardt et al. (1987) *Escherichia coli* and *Salmonella typhimurium*: Cellular & Molecular Biology (American Society for Microbiology, Washington D.C.), pp. 1071–1109.

Struhl (1981) Proceedings of the National Academy of Sciences, vol. 78, pp. 4461–4465.

Furuichi et al. (1985) Journal of Bacteriology, vol. 164, pp. 270–275.

Guyer (1983) Methods in Enzymology, vol. 101, pp. 362–369.

Life Technologies Catalog and Reference Guide. pp. 11–37 and 12–114 1993.

Wang et al., "Creating Nested Deletions for Sequencing Cosmid DNAs," Focus 15(2):47–49 (1993).

*Primary Examiner*—James Ketter
*Assistant Examiner*—Irem Yucel
*Attorney, Agent, or Firm*—Hamilton, Brook, Smith & Reynolds, P.C.

[57] ABSTRACT

The present invention discloses a rapid method of restriction mapping, sequencing or localizing genetic features in a segment of deoxyribonucleic acid (DNA) that is up to 42 kb in size. The method in part comprises cloning of the DNA segment in a specialized cloning vector and then isolating nested deletions in either direction in vivo by intramolecular transposition into the cloned DNA. A plasmid has been prepared and disclosed.

19 Claims, 4 Drawing Sheets

TRANSPOSON-CONTAINING DNA CLONING VECTOR AND USES THEREOF

This application is a continuation-in-part of application Ser. No. 08/057,314 filed on May 4, 1993, abandoned which is incorporated herein by reference in its entirety.

GOVERNMENT SUPPORT

This invention was made with Government support under Grant nos. DE-FG02-89ER-60862 and DE-FG02-90ER-610 by the Department of Energy. The Government has certain rights in the invention.

BACKGROUND

It is known that certain complex DNA segments, known as transposons, are able to insert into many sites in the genome of their host organisms. Transposons exist in prokaryotes, such as bacteria, as well as in eukaryotes.

Recently, a useful bacterial transposon referred to as γδ, or Tn1000, was discovered and characterized. γδ is a discrete six kilobase (kb) segment of bacterial DNA which can insert at high frequency into numerous sites in the plasmids of gram negative bacteria. It encodes the enzyme (transposase) for its own transposition, the enzyme (resolvase) for resolution of the cointegrate product that is produced by intermolecular transposition, and another gene, the function of whose product is unknown. The DNA sequence of γδ has been deposited in GenBank by R. Reed.

Further background information on γδ and related transposons can be had by reference to the recent review articles by Guyer, Meth. Enzymol. 101:362–363 (1983); Berg and Berg, Uses of transposable elements and maps of known insertions. In: Neidhardt, et al., (eds.), *Escherichia coil* and *Salmonella typhimurium:* Cellular and Molecular Biology. Amer. Soc. for Microbiology, Washington, D.C. pp. 1071–1109 (1987); Berg, Berg and Groisman, Transposable elements and the genetic engineering of bacteria. pp. 879–925. In: Berg and Howe (eds.), Mobile DNA. Amer. Soc. for Microbiology, Washington, DC.(1989); Sherratt, Tn3 and related transposable elements: Site-specific recombination and transposition. pp163–184 In: Berg and Howe (eds.), Mobile DNA. Amer. Soc. for Microbiology, Washington, D.C. (1989), and Berg et al., Transposon-facilitated sequencing of DNAs cloned in plasmids. Meth. Enzymol. 218:279–306 (1993).

Two widely used methods for DNA sequence analysis are the base-specific chemical cleavage method (Maxam and Gilbert, PNAS 74:560, 1977) and the enzymatic chain termination method (Sanger et al., PNAS 74:5463, 1977). The enzymatic chain termination method has gained wide acceptance as the method of choice. Generally in this method the DNA segment of interest is cloned in an appropriate vector and a short oligonucleotide complementary to a sequence adjacent to the cloning site is used to prime DNA chain terminators. Typically, only a few hundred base pairs (bp) can be sequenced from the primer site. Usually the sequence of longer DNA stretches is assembled from numerous random shod DNA sequences with the aid of computers. Further background information on dideoxy sequencing can be had by reference to the recent book by Sambrook et al. ( Molecular Cloning, Cold Spring Harbor Press, 1989).

The strategies to bring more distant DNA regions near to the primer site include: i) subcloning small DNA fragments into a plasmid, as noted above; ii) isolating nested deletions derivatives in vivo in a transposon vector (Ahmed, J. Mol. Biol. 178:941–948,1984; Meth. Enzymol. 155:177–204, 1987); iii)isolating nested deletions derivatives in vitro in a plasmid vector with appropriate restriction sites (Henikoff, Gene 28:351–359, 1984); iv) making new oligonucleotide primers complementary to the end of each sequenced segment (primer waking) (Winnoto et al., Nature 324: 679, 1986); or v) using random insertions of transposons into the chromosome or a large cloned piece of DNA (Adachi, et al., Nucleic Acids Res. 15: 771, 1987; Liu et al., Nucleic Acids Res. 15:9461–9469, 1987; Chow and Berg, PNAS 85: 6468–6472; Nag et al., Gene 64: 135–145, 1988; Phadnis et al., PNAS 86: 5908–5912, 1989; Strausbaugh et al., PNAS 87:6213–621 7,1990).

Major problems associated with each of these methods are summarized here: i) Subcloning is inefficient and often does not yield complete coverage, even with many-fold redundant sequencing, and aligning short DNA sequence fragments is sometimes difficult, especially if the clone contains repeated sequences. ii) Previously described vectors for isolating nested deletions into cloned DNA in vivo depend on intramolecular transposition by the transposon Tn9. These vectors contain the plasmid replication origin exterior to the transposon, between the transposon and cloned fragment. Consequently, deletions that extend into the cloned fragment in one direction are not recoverable because they delete the plasmid replication origin. Therefore, a second clone with the fragment in the opposite orientation must be used to access the other strand. In addition, Tn9 transposes nonrandomly, making it difficult to achieve complete coverage. iii) Previously described vectors for isolating nested deletions in vitro depend on the ability of specific exonucleases to digest DNA cleaved in a specific way. This process is often difficult to control and cannot readily be used to isolate deletions that extend more than a few kb from the deletion site. iv) Primer walking is a generally reliable method, but it is slow and expensive. In addition, it may be difficult to design unique primers for regions containing repeated sequences. v) Random insertions of a transposon can be done by very simple steps using in vivo reactions in *Escherichia Coil* cells, but insertion sites are difficult to map, and there is no way to select for insertions in a specific region. This invention avoids or minimizes many of the above described limitations.

Short DNA sequences that serve as initiation sites for replication (replication origins) are found in every autonomously replicating unit (replicon). Bacterial plasmids are small (generally up to 150 kb) replicons that are not absolutely required for bacterial growth under most conditions. Naturally occurring plasmids contain a replication origin, and other genes or genetic information, often including transposons. Natural transposons found in *Escherichia Coli* and related bacteria do not contain replication origins. Plasmid replication origins have, however, been cloned between the ends of transposons on a plasmid for various purposes, including to study the process of transposition (Cohen et al., Cold Spring Harbor Symp. Quant. Biol. 43: 1269–1255,1978); to insert the transposon into chromosomal DNA in vivo and then to clone DNA adjacent to the transposon insertion site either in vitro (Yakobson and Guiney, J. Bacteriol. 160:451–453, 1984; Furuichi et al., J. Bacteriol. 164:270–275, 1985; Koncz et al., Mol. Gen. Genet. 207:99–105, 1987) or in vivo (Groisman et al., PNAS 81:1480–1483); and for undefined uses (Mizuuchi et al., U.S. Pat. No. 4,716,105, 1987).

SUMMARY OF THE INVENTION

The use of nested deletions produced in vivo to place unique sites at different locations in cloned DNA has great potential value in molecular genetics. However, all previously described vectors for producing nested deletions in vivo suffered from two significant disadvantages: i) viable deletion products that end in the cloned fragment could be isolated in only one direction because deletions that extend in the other direction lack a plasmid replication origin and are inviable. ii) Tn9, the transposon used, transposes nonrandomly into most cloned fragments, making it difficult to obtain deletions with well-distributed endpoints.

The problem of not being able to recover intramolecular transposition deletion plasmids in which the deletion occurred in either direction, has been solved in this invention by placing the replication origin interior to the ends of a transposon that transposes replicatively.

The problem of the nonrandom distribution of deletion endpoints has been addressed by using a transposon (γδ, [gamma delta] also known as Tn1000) that usually transposes more randomly than other known transposons.

It is an object of the present invention to provide an in vivo method for the rapid mapping and sequencing of DNA segments cloned in a specialized transposon-containing vector, without subcloning.

It is another object of the present invention to provide a convenient and efficient method of sequencing large segments of DNA, particularly DNA segments greater than about 2 kb.

It is further object of the present invention to provide a plasmid having a specialized mini-γδ transposon containing a plasmid replication origin between the ends of the transposon, and bracketed by pairs of conditional lethal and selectable genes in a particular configuration in the plasmid in order to efficiently select deletion derivatives in which the deletion extends into the cloned fragment in either one direction or the other, and that does not extend beyond the cloned fragment.

The resulting cloning vector is the first vector designed for the simple in vivo production and recovery of random deletions that extend in either direction from the transposon into the cloned DNA for the purposes of restriction mapping and of delivering unique sites to different segments of the target DNA. The unique sites, so delivered, are used to prime DNA sequencing reactions, to sequence all or part of the cloned fragment, to prime RNA synthesis to make RNA transcripts complementary to DNA sequences adjacent to either the cloning site or the transposon end, and for other uses.

Restriction fragment patterns obtained from the parental plasmid and the deletion derivatives are used to rapidly create high quality restriction maps of the cloned fragment with this same vector.

Other objects and advantages of the present invention will become apparent as the detailed description of the invention proceeds.

BRIEF DESCRIPTION OF THE DRAWINGS

These and other objects, features and many of the attendant advantages of the invention will be better understood upon a reading of the following detailed description when considered in connection with the appended claims, description and accompanying drawings wherein:

Figure 1:
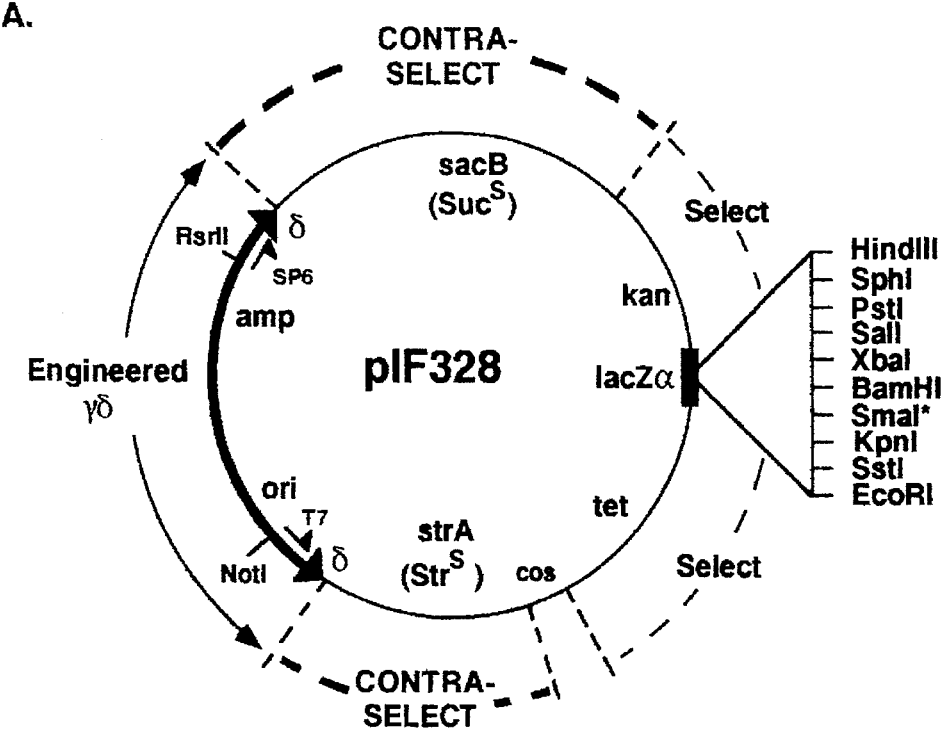
FIG. 1 is a diagrammatic representation which shows the structures of two min1-γδ-ori plasmids. pIF328 pDUAL-1 is a preferred embodiment of the invention which has been reduced to practice (FIG. 1A). The plasmid depicted in FIG. 1B lacks amp and has unique sites (labeled X and Y) for the initiation of RNA transcription bracketing the cloning site. ori is the plasmid replication origin; amp, kan and tet confer resistance to ampicillin, kanamycin and tetracycline, respectively (selectable genes); sacB and strA (also called rpsL) confer sensitivity to sucrose and streptomycin, respectively (conditional lethal or contraselectable genes); cos is the bacteriophage λ cos (cohesive ends) site; lacZα is the alpha fragment of the lacZ gene that has been engineered to contain a number of unique restriction sites; NotI and RsrII are two additional unique restriction sites interior to the transposon ends; T7 and SP6 are promoters from the bacteriophages T7 and SP6 that are used to produce RNA transcripts; X and Y are different promoters from bacteriophages that are used to produce RNA transcripts; δ indicates the 40 bp delta ends of γδ.
Figure 1:
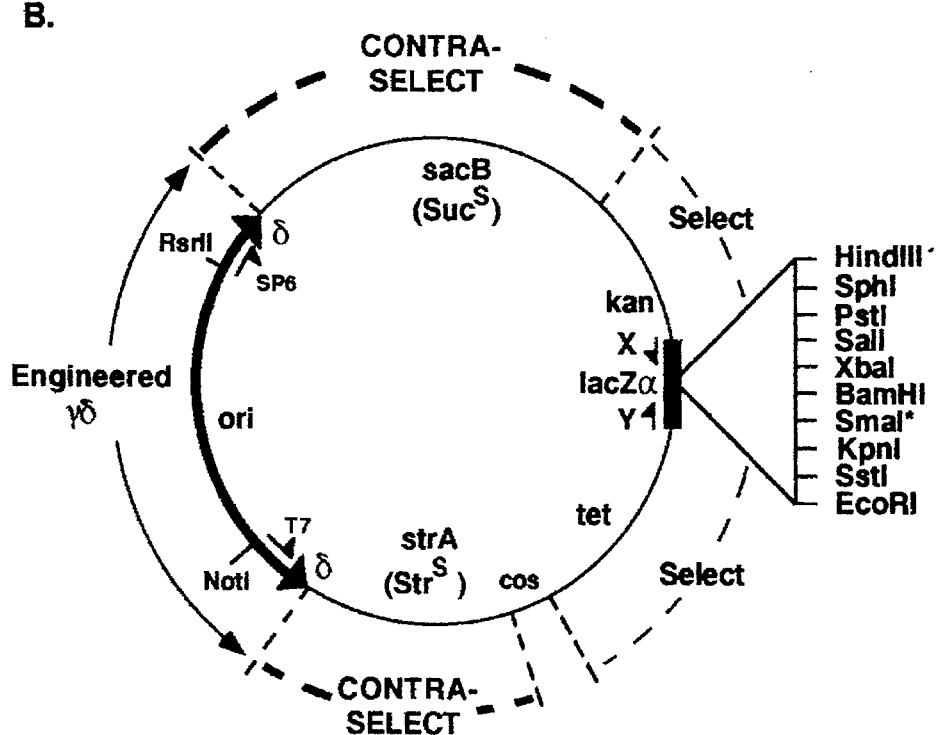

Different restriction enzymes and combinations of restriction enzymes will, of course, yield different sized restriction fragments, but the dropout patterns will be complementary (they will form an internally consistent restriction map in which the restriction sites for all enzymes used are unambiguously located). It should be noted that in the case of restriction enzymes that do not cut the transposon component, or cut internal to its ends, the fragment that contains the insertion (and consequently contains less cloned DNA) may be larger than intact fragment.

DETAILED DESCRIPTION OF THE INVENTION

The terms transposon, transposition, intramolecular, oligonucleotide, clone, ligate, prime, primer, vector, plasmid, gene, genome, marker, γδ, restriction enzyme, RNA, RNA transcript, bp, kb, selectable, contraselectable, induction, conditional lethal, cos and the like as used herein are defined to convey their well established ordinary meaning in the art to which they pertain and may be found in many modern textbooks or publications related to molecular or biochemical genetics and genetic engineering, the same being incorporated herein by reference. Preferable among such publications are Berg and Howe, supra; Berg et al., 1993, supra; Sambrook supra, which is incorporated herein by reference.

The term "mini-γγ'" as used herein is defined as a segment of DNA that retains the capability to function as a γδ transposon (a minimum of 35–38 bp in inverted orientation from either or both ends of transposon γδ).

The term replicon is used in its original meaning in the art to describe a genetic element that behaves as a unit of DNA replication.

These and other objects and advantages of the present invention are achieved by providing a plasmid having some or all of the following features:

i) the terminal sequences needed for transposition of a replicatively transposing transposon, such as the 40 bp from the δ end of γδ present in pIF328;

ii) a plasmid replication origin between the transposon ends, such as the pUC19 plasmid origin present in pIF328 (this is all that is absolutely required to use this vector);

iii) a pair of conditional lethal (contraselectable) genes immediately outside the transposon ends, such as the strA (rpsL) and sacB genes present in pIF328;

iv) a pair of selectable genes outside of the conditional lethal genes, such as the tet and kan genes present in pIF328;

v) a selectable gene between the ends of the transposon, such as the amp gene present in pIF328;

vi) a gene or segment between the selectable or conditional lethal genes outside of the transposon containing restriction enzyme digestion sites for in vitro cloning, such as in the lacZα fragment from pUC19 present in pIF328;

vii) a cosmid cloning (cos) site for in vitro cosmid cloning of large (30–42 kb) fragments, such as is present in pIF328.

viii) a pair of unique sites just interior to the transposon ends, which are designed for binding of DNA sequencing primers, such as are present in p! F328.

ix) pairs of rare restriction enzyme digestion sites just interior to the transposon ends for producing nested deletions in vitro.

x) a pair of unique bacteriophage promoter sequences just interior to the restriction sites described in (ix), if present, or just interior to the transposon ends for the synthesis of RNA transcripts of adjacent DNA, such as is present in pIF328.

xi) a pair of unique bacteriophage promoter sequences bracketing the cloning site for the synthesis of RNA transcripts of adjacent cloned DNA.

xii) a cloning site for in vitro cloning.

The type of transposon useable for this invention is limited to a transposon that transposes replicatively, but is, of course, not limited to γδ However, the preferred use of the mini-γδ transposon has an advantage over most other replicatively transposing transposons because of its high frequency of transposition, the relative randomness of its transposition into most cloned fragments, and the ability of γδ transposase to catalyze efficient γδ transposition when synthesized from a transposase gene in a different plasmid. However, other replicatively transposing transposons that transpose efficiently and relatively randomly can also be employed. The detailed structure of the mini-γδ transposon is not critical. In the practice of the present invention, a mini-γδ transposon that carries a plasmid pUC19 replication origin and amp (ampicillin resistance) gene, and T7 and SP6 phage promoter sites are used (FIG. 1A), although a smaller mini-γδ with only the pUC19 or another plasmid origin (FIG. 1B), or a larger mini-γδ (not shown) with additional genes and restriction sites can also be used.

The placement of an origin of replication within the transposon is, however, critical since this feature permits deletions that extend from the transposon into the cloned fragment in either direction to survive and be recovered. Which origin of replication is used is not critical: for some purposes it may be advantageous to use an origin that maintains its host plasmid in high copy number or low copy number, or to use an origin that maintains its host plasmid under low copy number in some growth conditions and under high copy number in other growth conditions.

The vector component outside of the transposon component of the plasmid is also quite flexible, i.e., the invention is not restricted to the vector exemplified herein. A cloning site is required for cloning DNA fragments in vitro. Conditional lethal genes bracketing the transposon, either SacB and strA (rpsL) as used in this invention, or other such genes, are required for isolating deletions on selective bacteriological growth medium, but not if deletions are isolated electrophoretically by plasmid size on a gel. Selectable genes bracketing the contraselectable genes or transposon ends, either tet and kan as used in this invention, or other such genes, are required for isolating deletions on selective plates that do not extend beyond the cloned fragment, but not if deletions are isolated electrophoretically by plasmid size. However, the plasmid must contain at least one selectable gene, for plasmid maintenance. The cos site is required for cosmid cloning, but could be placed anywhere in the plasmid, including in the transposon.

The transposase gene is cloned in a compatible plasmid in the current usage, although it could also be present in the host chromosome.

FIG. 1A embodies the essential features of the transposon-vector system described herein that has been reduced to practice, and FIG. 1B embodies one alternate form in which no antibiotic resistance gene is present between the ends of the transposon, and in which sites for the intiation of unique RNA transcripts have been placed bracketing the cloning site.

Figure 2:
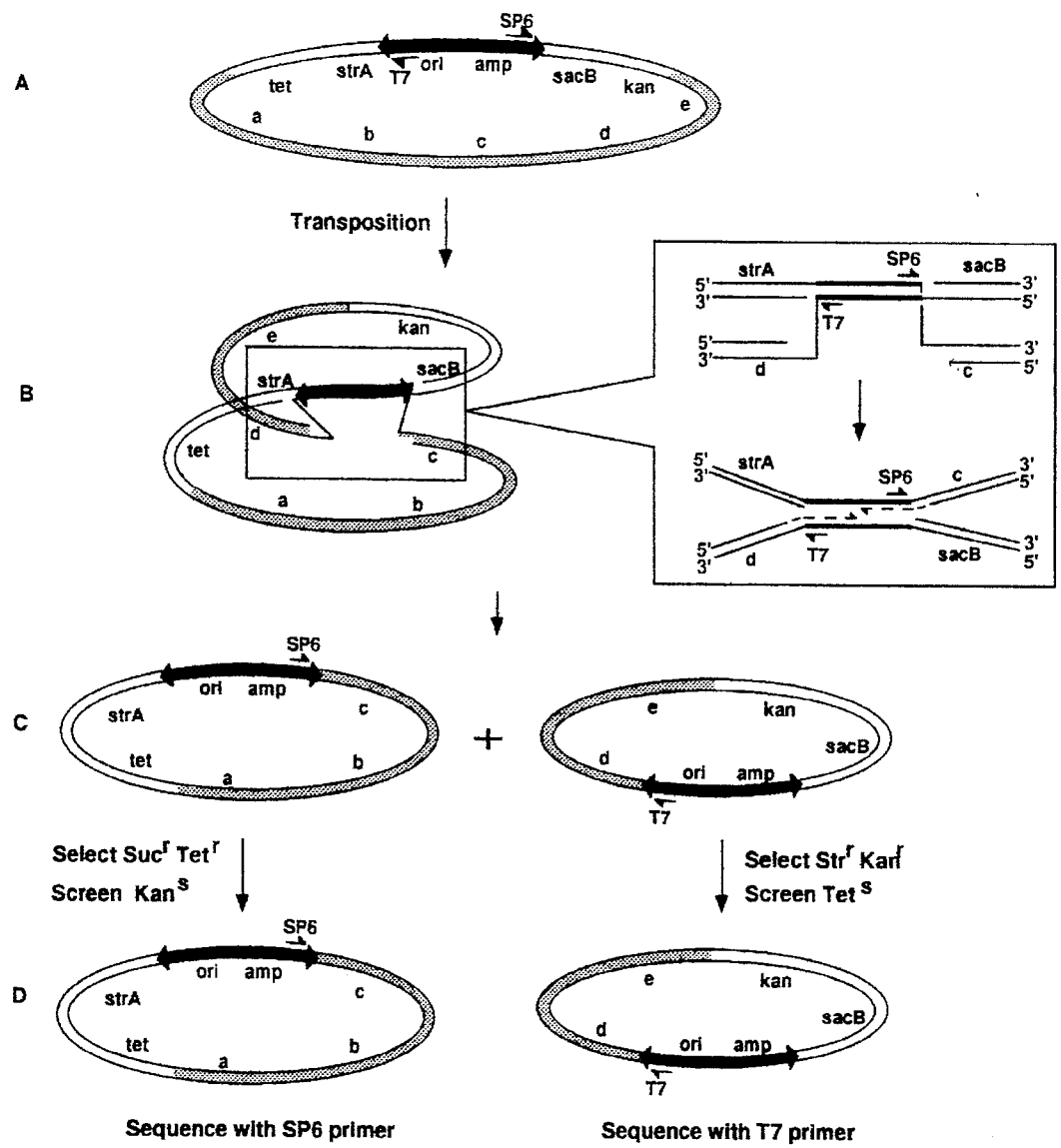
FIG. 2 is a diagrammatic representation of intramolecular transposition to yield deletion derivatives (inversion derivatives not shown) in a plasmid in which a DNA fragment (a, b, c, d, e) was cloned into pIF328 (FIG. 1).

Intramolecular transposition may occur in either of two orientations to give inversion (not shown) or deletion products, as depicted in FIG. 2. Upon induction of transposition, the ends of the transposon are thought to form a complex with target DNA, cleave the target DNA at staggered sites and the transposon at its 3' termini, ligate the transposon and target, and replicate the transposon and single stranded target DNA as depicted in FIG. 2B. Transposition may occur between the transposon and target DNA on different molecules (intermolecular transposition) or in the same molecule (intramolecular transposition). Only the intramolecular deletion products are relevant to the applications described herein. Deletion formation is believed to be a reciprocal process, in which each transposition event yields two exact reciprocal products (containing the a-c and d-e segments), each with a copy of γδ that has one end at the insertion site, as depicted in FIG. 2C, plus a five bp duplication of the target site. Only one transposition product is recovered in this instance because of the selection for Suc$^r$ or Str$^r$ (FIG. 2D), and plasmid segregation. However, for previously described vectors, that do not contain a replication origin between the transposon ends, one of the deletion products lacks a replication origin and is therefore inviable. For vectors, such as pIF328, that contain the replication origin between the transposon ends, one of the expected deletion products is also lost because of normal segregation without selection for maintanence of that vector (in addition, that deletion product is usually selected against by presence of a conditional lethal gene on it). However, both products are potentially viable, and which one is recovered depends upon the selection imposed. An *E. coli* host cell containing pIF328 has been deposited with the American Type Culture Collection, 12301 Parklawn Drive, Rockville, Md. 20852, and has been assigned Accession No. 98161 Sep. 6, 1996.

Figure 3:
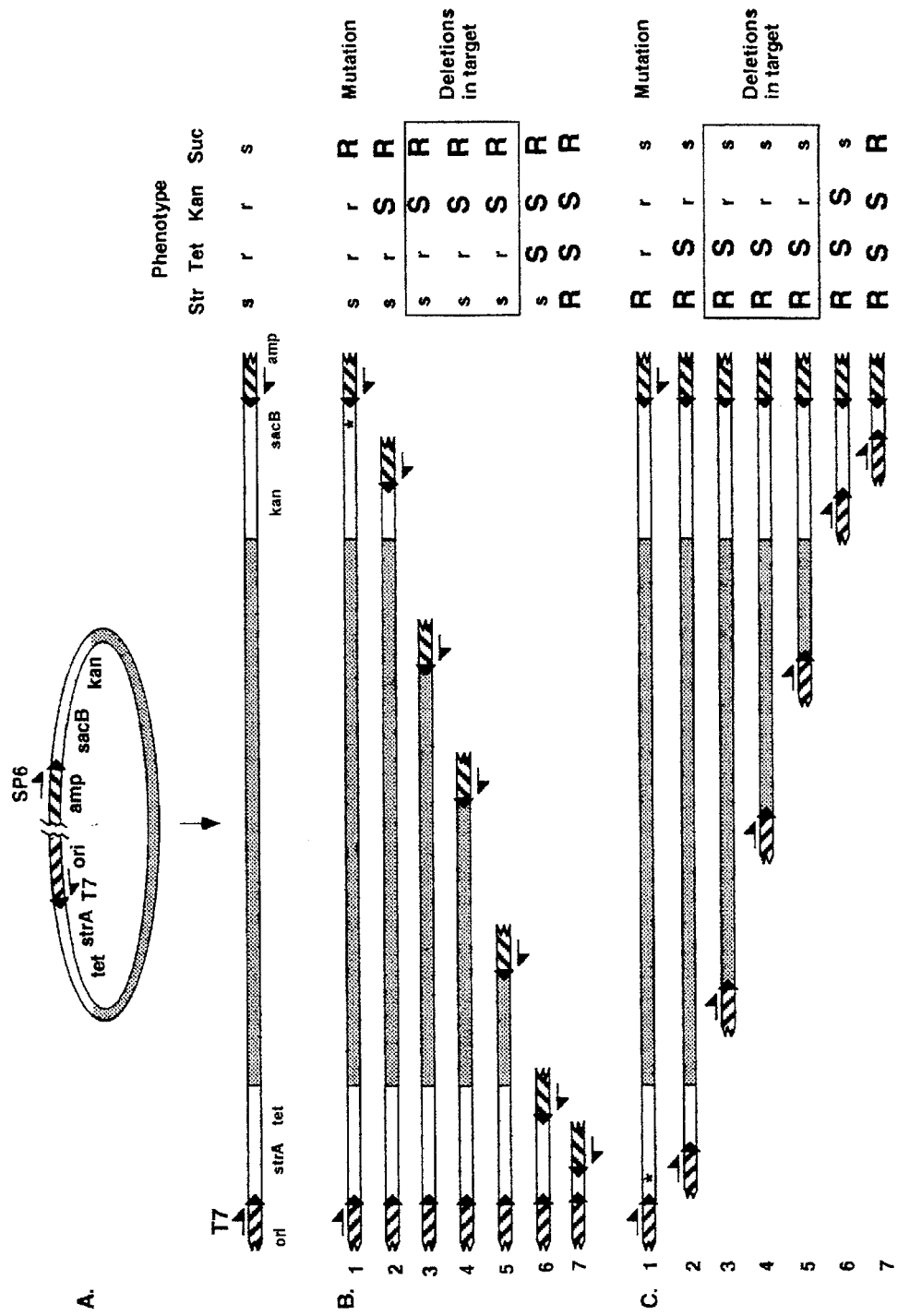
FIG. 3 is a diagrammatic representation which shows the types of deletion derivatives expected after plating cells containing a pIF328 clone on selective media, and the phenotypes the deletion plasmids confer on their host cells. Intramolecular transposition and selection for $Suc^r$ (panel B) or $Str^r$ (panel C) yields deletions of various sizes, whose phenotypes are indicated. The changes in phenotype are marked by large capitol letters, with the deletions that have insertions into the cloned fragment (#s 3, 4, 5) being boxed.

As diagrammed in FIG. 3., a subset of the intramolecular transposition products will confer resistance to sucrose or streptomycin, as a result of deletion of the sacB$^+$ (confers sucrose-sensitivty) or strA$^+$ (rpcL$^+$) (confers streptomycin-sensitivity) genes, respectively. When a large DNA fragment has been cloned in the cloning site, a majority of the deletions will extend into this DNA fragment. To preclude recovering derivatives in which the deletions extended beyond this cloned fragment, only those derivatives that retain resistance to tetracycline (among sucrose-resistant colonies) or kanamycin (among streptomycin resistant colonies) are sought, by plating cells on medium containing sucrose plus tetracycline or on medium containing streptomycin plus kanamycin. Screening for kanamycin-sensitivity among sucrose plus tetracycline-resistant clockwise deletion colonies and for tetracycline-sensitivity among streptomycin plus kanamycin-resistant counterclockwise deletion colonies ensures that only deletion derivatives, most of which extend into the cloned fragment, are analyzed.

Figure 4:
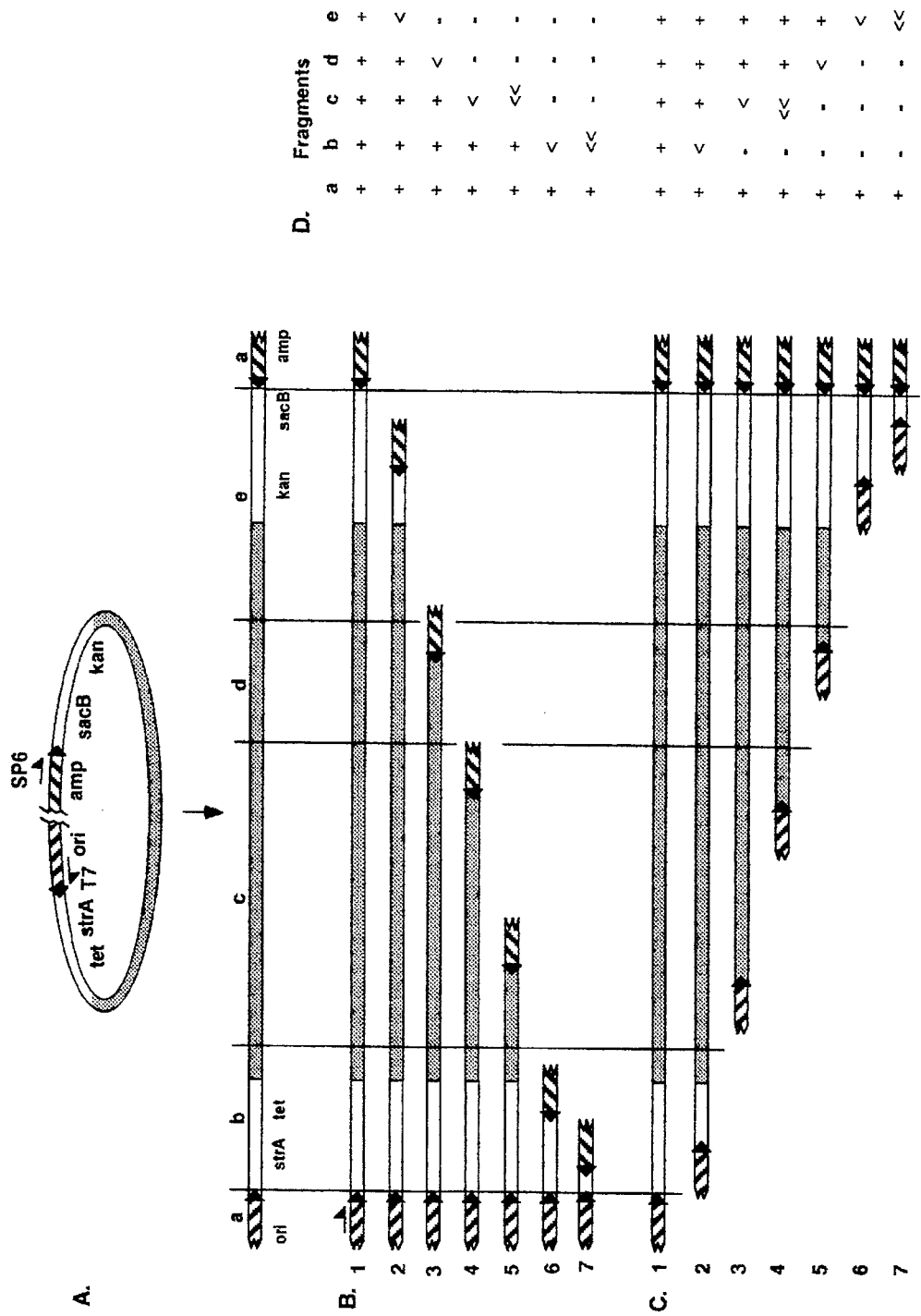
FIG. 4. is a diagrammatic representation which shows how restriction sites in the cloned fragment are ordered (mapped) using deletion plasmids FIG. 3) in a "dropout analysis". The restriction sites are marked by vertical lines, the fragments are marked a-e. Fragment a, in this example, represents the transposon component, which is retained without change in size in all deletion plasmids, fragments b and e contain both vector and cloned segment sequences, while fragments c and d contain only cloned segment sequences. + indicates that the fragment is unchanged in size, < that the fragment is smaller, << that the fragment is much smaller, and − that the fragment is completely absent.

As diagrammed in FIG. 4, the locations of restriction sites that are digested by specific enzymes are readily determined by digesting the parental clone and a set of the intramolecular transposition products with that enzyme and analyzing the resultant DNA fragments on an agarose gel. For illustrative purposes, the clone and deletion derivatives shown in FIG. 4 are digested by an enzyme at five sites, to yield five fragments of unequal sizes (a-e) upon agarose gel electrophoresis. Digestion with different enzymes singly, and in combination, yields additional information (not shown). FIG. 4D diagrams the "dropout" pattern of restriction fragments obtained using a restriction enzyme that cuts at each transposon end and at three additional sites. It is clear from this example that a deletion that extends into the DNA between two restriction sites yields a truncated restriction fragment, while a deletion that extends beyond the farthest site deletes the fragment entirely. Thus the restriction sites in the deletions derivatives can be located by information on the selection imposed and the dropout pattern, even if restriction sites are not present in the vector, or are situated asymmetrically.

The unique property of this invention is the ability of plasmids that have deletions that extend from either transposon end into the cloned fragment to survive. This property is due to the location of the essential replication origin between the transposon ends, so that all of the vector DNA, outside of the transposon is dispensable.

To efficiently obtain a restriction map of the cloned fragment, a small set of clockwise and of counterclockwise deletion plasmids (perhaps 5-20) are isolated as described above. The sizes of these plasmids are determined, or selected, by isolation of plasmid DNA by standard methods and electrophoresis of plasmid DNA from single colonies, or from pools of many colonies in an agarose gel. Large plasmids have small deletions, and vice versa. One or more restriction enzymes that cleave the clone into two or more fragments after single or double digestion are used to cleave the DNA from the parental clone and from the deletion plasmids as depicted in FIG. 4. In this "drop out" analysis, these unordered fragments, that reflect pairs of restriction sites, are ordered by correlating plasmid size with the presence or absence of the fragment, or the presence of a fragment of altered size.

To obtain sequence information from the target DNA, DNA sequencing reactions are run using DNA isolated from appropriate deletion plasmids, using a primer that binds to the primer binding site that has been moved adjacent to target DNA by intramolecular transposition, i.e., using the SP6 primer for clockwise deletions or the T7 primer for counterclockwise deletions (FIG. 1). From this stage on, this method uses the base-specific chain terminator method of Sanger et al., supra, for DNA sequence determination reactions, and the standard gel electrophoresis method for the resolution of the reaction products in order to read the sequence is used.

To produce RNA transcripts from the phage promoters, standard methods are used, as described in Sambrook, et al., supra.

Heretofore, all methods of producing the library of subclones needed for the base specific chain termination method of Sanger et al supra, required in vitro insertion of subfragments into a cloning vector DNA, transposon hopping into cloned DNA, in vitro production of nested deletion subclones, or in vivo production of nested deletions in two different plasmids with the fragment cloned in opposite orientations. Since the process embodied in this invention utilizes efficient in vivo intramolecular transposition reaction in both the clockwise and counterclockwise directions, it can be carried out by a simple plating on appropriate selective media, and mapping of insertion sites can be accomplished merely by determining the size of the deleted plasmid. Each member of the library carries a deletion plasmid in which a transposon end and adjacent primer binding site is next to target DNA. The point of insertion is usually quite random. The entire process of in vivo transposition and plating for colonies carrying deletion plasmids is carried out in a few hours. On the next day, each colony is grown, DNA is prepared and the sequence reactions and gel electrophoresis can be carried out.

In addition, one can also map the point of mini-γδ insertion (deletion site) in each deletion plasmid by agarose gel electrophoresis of double stranded plasmid DNA, or of linearized DNA digested by one or more restriction enzymes (which also yields a restriction map of the fragment).

In addition, after most of the sequence of the fragment has been determined, the gaps in the sequence can be closed in a directed manner by selecting deletion derivatives of the appropriate sizes after agarose gel electrophoresis.

The library of deletion derivatives obtained in accordance with the present invention is useful for other purposes in addition to the production of restriction maps and DNA sequences described above. For example, it can be used to localize genes by inactivation, as an intermediate for trimming purposes, or to produce RNA transcripts for segments within the fragment. The *Escherichia coli* host strain containing the plasmid pIF328 (PDUAL-1) was deposited on Dec. 17, 1993 with the American Type Culture Collection (ATCC), 12301 Parklawn Drive, Rockville, Md. 20852. This deposit was assigned ATCC Accession No. 47073.

MATERIALS AND METHODS

Strains and general techniques. Plasmid pXRD4043, which contains the γδ transposose gene cloned downstream of a tac promoter in plasmid pACYC184 (Tsai et al., J. Bacteriol. 169: 5556-5562), was used to provide a high level of transposase. Control experiments indicated significant constitutive transposase synthesis in the strains used, and hence IPTG (to further induce transcription from tac) was usually not added. Resolvase did not have to be provided because no cointegrate step is involved in deletion formation (FIG. 2).

The *E. coli* K-12 host strain used for isolating nested deletions in pIF328 must be sensitive to ampicillin, kanamycin, tetracycline and chloramphenicol and resistant to streptomycin (all strA [rpsL] strains) and sucrose (most E. Coli K-12 strains). It should also be: recA, to maintain the plasmid as a monomer and to increase the stability of cloned fragments; readily transformable; and contain a highly expressed γδ transposase gene.

Plasmid DNA was prepared by a miniprep method. DNA extraction and recombinant DNA cloning were performed using standard methods (Sambrook et al., supra). PCR and linear amplification (cycle) sequencing (BRL) were done using a Perkin-Elmer thermal cycler model 480. Standard chemicals and reagents were from Gibco/BRL or Sigma. Gelase was from Epicentre Technologies.

Appropriately supplemented L broth (LB) and L agar (LA) (sometimes NaCl-free) were used for bacterial growth and selection of deletion derivatives.

Antibiotics were used at the following concentrations: ampicillin (Amp), 100 µg/ml; chloramphenicol (Cam), 15–30 µg/ml; kanamycin sulfate (Kan), 25–50 µg/ml; streptomycin (Str), 100 µg/ml; and tetracycline (Tet), 15 µg/ml; Methicillin, 100 µg/ml, was usually added to Amp-selection plates to reduce the background growth of $Amp^s$ cells in some experiments (4). Sucrose (Suc) was used at 5%.

To isolate plasmids or fragments of specific sizes, DNA was electrophoresed in 0.5–0.7% low melting point agarose, cut from the gel, and digested with 1–2 units of gelase per gram of gel for one to two hours.

Construction of pIF328. This 7.9 kb cosmid cloning vector (FIG. 1) was constructed using standard recombinant DNA and PCR methods (Sambrook et al., supra). Site-directed mutagenesis (to remove unwanted restriction sites) was done using the T7-GEN In Vitro Mutagenesis kit (USB).

DNA sequencing. Plasmid DNA was sequenced using the dsDNA Cycle Sequencing kit (BRL). The primers used were:

SP6, 5'-ATTTAGGTGACACTATAG-3' (SEQ ID NO. 1);

T7, 5'-TAATACGACTCACTATAGGG-3' (SEQ ID NO. 2).

Selection and screening of deletion plasmids. Several protocols were used in initial tests of pIF328 clones, and several are recommended, depending on whether a directed, random, or screening protocol is preferred.

1. Directed sequencing strategy i). Transform the pIF328 clone into a recA, strA (rpsL) strain that contains the transposase helper plasmid pXRD4043, selecting for $Kan^r$ $Tet^r$ $Cam^r$ and screening for Strs Sucs colonies (or transform the 5.4 kb pXRD4043 plasmid into a recA StrA (rpsL) strain that contains the pIF328 clone).

ii). Spread cells from overnight cultures grown in (a) L broth (LB) plus Tet and Cam (no Suc) and (b) LB plus Kan and Cam (no Str) onto (a) L agar (LA) plus Tet and Suc, and (b) LA plus Kan and Str, to select clockwise and counterclockwise deletions, respectively. Incubate overnight at 37° C.

iii) Scrape each selection plate, isolate plasmid DNA, and fractionate in low melting point agarose.

iv) Slice gels into 1–2 kb size fractions, transform a recA strA strain (without the transposase plasmid, pXRD4043) and plate samples from (a) and (b), above, on (a) LA plus Tet and Suc for clockwise deletions, or on (b) LA plus Kan and Str for counterclockwise deletions.

v). Pick several individual transformants from each fraction, and isolate plasmid DNA.

vi) Sequence target DNA using the SP6 promoter primer for clockwise deletions, and the T7 promoter primer for counterclockwise deletions. Notes:

1. Cam, which selects for the transposase helper plasmid pXRD4043, should be included in the medium in steps (i) and (ii), but not in step (iv).

2. Care must be taken to avoid overloading gel in step (iii); otherwise a significant fraction of the plasmids recovered may be smaller than expected.

2. Shotgun Sequencing Strategy i and ii) As above.

iii). Pick individual colonies from selection plates and isolate plasmid DNA (usually, more than 95% of the $Tet^r$ colonies are $Kan^s$, or vice versa, and have plasmids with deletion endpoints in the target DNA, making further screening unnecessary).

iv) As step vi, above.

Once sufficient coverage is achieved, the ends of contigs should be mapped by size of the corresponding plasmids, and the gaps filled by size-fractionating large pools of $Suc^r$ $Tet^r$ or $Str^r$ $Kan^r$ colonies, as described above.

3. Colony sreening strategy i and ii) As above.

iii). Pick individual colonies from selection plates and spot on media containing each of the antibiotics and conditional lethal selective products individually.

iv) Isolate plasmid DNA from colonies that are $Suc^r$ $Tet^r$ $Kan^s$, and from colonies that are $Str^r$, $Kan^r$ $Tet^s$, and electrophorese in low melting point agarose to rough-map deletion endpoints.

v) Choose an appropriate array of plasmids (large plasmids may have to be cut for accurate sizing), and sequence target DNA using the SP6 promoter primer for clockwise deletions, and the T7 promoter for counterclockwise deletions.

It is understood that the examples and embodiments described herein are for illustrative purposes only and that various modifications or changes in light thereof will be suggested to persons skilled in the art and are to be included within the spirit and purview of this application and the scope of the claims.

We claim:

1. A double stranded DNA cloning vector comprising:
   a) a transposon containing an origin of replication, said transposon being flanked by two contraselectable genes that are different from one another; and
   b) a cloning site inserted between the two contraselectable genes and exterior to the transposon.

2. The cloning vector of claim 1, wherein the cloning site is flanked by two selectable genes that are different from one another.

3. The cloning vector of claim 1, wherein the transposon further contains a selectable gene.

4. The cloning vector of claim 1, wherein the transposon further contains unique primer binding sites interior to each end of said transposon.

5. The cloning vector of claim 1, further comprising a cos site for cosmid cloning.

6. The cloning vector of claim 1, wherein said transposon is constructed from two ends of transposon gamma delta in inverted orientation.

7. The cloning vector of claim 1, wherein the transposon further contains unique RNA transcription initiation sites interior to each end of said transposon.

8. The cloning vector of claim 1, further comprising unique RNA transcription initiation sites flanking said cloning site.

9. A bacterial host cell containing the DNA cloning vector of claim 1.

10. An *Escherichia coli* host cell containing plasmid pIF328, which host cell is deposited at the American Type Culture Collection as ATCC Accession No. 98161.

11. Plasmid pIF328 contained in the *Escherichia coli* host cell deposited at the American Type Culture Collection as ATCC Accession No. 98161.

12. A method of delivering unique primer binding sites randomly into a cloned DNA segment, utilizing both strands of the DNA segment, comprising:
   a) introducing a double-stranded DNA vector into an appropriate host cell, said vector comprising:
      i) a transposon containing an origin of replication and unique primer binding sites, said transposon being flanked by two contraselectable genes that are different from one another;
      ii) a cloning site inserted between the contraselectable genes and exterior to the transposon;
      iii) at least one selectable gene located within the transposon, or two selectable genes which flank the cloning site and are different from one another, or both; and
      iv) a cloned DNA segment located in the cloning site, wherein the host cell expresses a transposon transposase gene such that sets of intramolecular transposition deletion products are produced;
   b) selecting, in either orientation, sets of intramolecular transposition deletion products using an appropriate pair of selection conditions, such that one of the primer binding sites is introduced into the cloned DNA segment; and
   c) amplifying the intramolecular transposition deletion products selected in step b).

13. The method of claim 12, further comprising determining the size of the selected deletion products to locate the transposed transposon end in the cloned DNA segment.

14. The method of claim 12, further comprising sequencing the DNA segment from the primer binding sites.

15. The method of claim 12, wherein the transposon further contains RNA transcription initiation sites.

16. The method of claim 15, further comprising generating RNA transcripts complementary to the DNA segment from the RNA transcription initiation sites.

17. The method of claim 12, wherein step (a) is performed by transformation, transduction or electroporation.

18. A method of ordering restriction fragments from a cloned DNA segment, comprising:
   a) introducing a double-stranded DNA vector into an appropriate host cell, said vector comprising:
      i) a transposon containing an origin of replication and unique primer binding sites, said transposon being flanked by two contraselectable genes that are different from one another;
      ii) a cloning site inserted between the contraselectable genes and exterior to the transposon;
      iii) at least one selectable gene located within the transposon, or two selectable genes which flank the cloning site and are different from one another, or both; and
      iv) a cloned DNA segment located in the cloning site, wherein the host cell expresses a transposon transposase gene such that sets of intramolecular transposition deletion products are produced;
   b) selecting, in either orientation, sets of intramolecular transposition deletion products using an appropriate pair of selection conditions, in which one of the transposon ends is introduced into the cloned DNA segment;
   c) amplifying the intramolecular transposition deletion products selected in step b);
   d) digesting the vector containing the cloned DNA segment using at least one restriction enzyme and determining the sizes of the restriction fragments;

e) digesting each member of a subset of the intramolecular transposition deletion products derived from the vector containing the cloned DNA segment using at least one restriction enzyme and determining the sizes of the restriction fragments in each;

f) comparing the sum of the sizes of the restriction fragments from each member of the subset of intramolecular transposition deletion products to the size of the parent clone and to the size of the intramolecular transposition deletion product from which the restriction fragments were recovered;

g) determining the order of disappearance of the restriction fragments from increasingly smaller deletion plasmid products; and h) determining the order of the fragments in the cloned DNA fragment.

19. A method of identifying the location of a selected genetic feature, comprising:

a) introducing a double-stranded DNA vector into an appropriate host cell, said vector comprising:

i) a transposon containing an origin of replication and unique primer binding sites, said transposon being flanked by two contraselectable genes that are different from one another;

ii) a cloning site inserted between the contraselectable genes and exterior to the transposon;

iii) at least one selectable gene located within the transposon, or two selectable genes which flank the cloning site and are different from one another, or both; and iv) a cloned DNA segment located in the cloning site, wherein the host cell expresses a transposon transposase gene such that sets of intramolecular transposition deletion products are produced;

b) selecting, in either orientation, sets of intramolecular transposition deletion products using an appropriate pair of selection conditions, in which one of the transposon ends is introduced into the cloned DNA segment;

c) amplifying the intramolecular transposition deletion products selected in step b); and d) testing increasingly smaller deletion products in either direction from the transposon for the presence of a selected genetic feature to determine in which deletion products the genetic feature is at least partially deleted, wherein the deletion product with at least partially deleted genetic feature is indicative of the location of the genetic feature.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear (xi) SEQUENCE DESCRIPTION: SEQ ID NO:1:

ATTTAGGTGA CACTATAG                                                                                    1 8

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

TAATACGACT CACTATAGGG                                                                                  2 0